United States Patent [19]

Bell et al.

[11] Patent Number: 4,689,126

[45] Date of Patent: Aug. 25, 1987

[54] METHOD OF CONVERTING A PRECURSOR CERAMIC SOLID INTO A SOLID CERAMIC HYDRONIUM CONDUCTOR

[75] Inventors: Michael F. Bell, Kingston; Patrick S. Nicholson, Ancaster; Michael Sayer, Kingston, all of Canada; Kimihiro Yamashita, Tokyo, Japan

[73] Assignee: Canadian Patents and Developments Limited, Ottawa, Canada

[21] Appl. No.: 673,937

[22] Filed: Nov. 21, 1984

[30] Foreign Application Priority Data

Dec. 20, 1983 [CA] Canada ................................. 433793

[51] Int. Cl.$^4$ ............................................. C25F 5/00
[52] U.S. Cl. .................................................. 204/130
[58] Field of Search ................................ 204/130, 140

[56] References Cited

U.S. PATENT DOCUMENTS 4,381,216  4/1983  Singh .................................. 156/667

Primary Examiner—T. M. Tufariello
Attorney, Agent, or Firm—Mitches & Co.

[57] ABSTRACT

A method of converting a feed solid polycrystalline of $\beta$ alumina into a hydronium conductor requires the preselection of an appropriate feed ceramic preferably with a chemical formula;

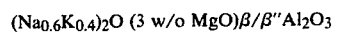

$(Na_{0.6}K_{0.4})_2O$ (3 w/o MgO)$\beta/\beta''Al_2O_3$ and with a $f(\beta)$ of $0.37 \pm 0.03$
wherein $$f(\beta) = \frac{\beta}{\beta + \beta''}$$

The crystallographic lattice is altered by placing the solid feed ceramic in an ionic solution or melt containing two or more ionic species of different ionic radii; the composition of the melt or solution being written: $M_1$, $M_2 (M_3 \ldots) X$ where $M_1$ and $M_2$ (and $M_3$ etc.) are ions of dissimilar size and as examples sodium, potassium, lithium and hydronium ions. After a time the material is removed, washed and subjected to a field effect exchange whereby the desired hydronium conducting solid ceramic having the following chemical composition is achieved;

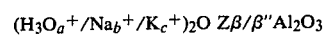

$(H_3O_a^+/Na_b^+/K_c^+)_2O\ Z\beta/\beta''Al_2O_3$ where (a)(b)(c)=0→1 and a+b+c=1 and Z is a stablizer of the $\beta''$ phase.

13 Claims, 6 Drawing Figures

METHOD OF CONVERTING A PRECURSOR CERAMIC SOLID INTO A SOLID CERAMIC HYDRONIUM CONDUCTOR

This invention relates to a novel ceramic conductor of the hydrogen specifically a solid polycrystalline $\beta$ alumina ceramic, and to a method for preparation of the same by transforming a precursor solid polycrystalline $\beta$ alumina ceramic.

Solid ionic conductors have been the subject of intensive research with respect to their use as separators in batteries, ion detectors, gas sensors, electrochromic displays and other electrochemical devices where their properties of high ionic conductivity with negligible electronic conductivity can be used to advantage.

A familiar group of compounds is based on the property of $\beta$ alumina to act as an ion exchanger. Thus a large number of derivatives such as the lithium, potassium, silver and hydronium analogues have been prepared by immersing *single* crystals of sodium $\beta$ alumina in appropriate ionic melts. However polycrystalline ceramics which would be formed into desired environmental shapes tend to degrade mechanically on ion exchange due to the stresses caused by lattice expansion (or contraction) on incorporation of ions of dissimilar size. The dimensional size of 2 relevant ions is given below;

$K^+ = 1.4$ Å
$Na^+ = 0.9$ Å

Some of the inventors herein have earlier disclosed in co-pending patent applications a mixed sodium/potassium compound, a method of preparing the same as a polycrystalline powder and subsequently a method of generating from the powder rigid polycrystalline ceramics. These applications are now entitled THE PREPARATION OF A PRECURSOR POWDER FOR THE MANUFACTURE OF A CERAMIC HYDROGEN ION CONDUCTOR [1], filed in Canada, Apr. 28, 1981 and THE PREPARATION OF A PRECURSOR SOLID FOR THE MANUFACTURE OF A CERAMIC HYDROGEN ION CONDUCTOR, filed in Canada, June 23, 1983. The resulting ceramics have a high density and a low proportion of $\beta$ phase. For convenience and for understanding, it is appropriate to define the following function for the proportion of $\beta$ phase; wherein $$f(\beta) = \frac{\beta}{\beta + \beta''}$$

It was the object of the previous inventions to achieve a high density, mechanically strong ceramic possessing $\beta$ alumina and $\beta''$ alumina phases where $f(\beta)$ is preferably $0.37 \pm 0.03$. The preferred compound is of chemical formula;

$$(Na_{0.6}K_{0.4})_2O(3w/oMgO)\beta/\beta''Al_2O_3$$

In order to explain the properties of such compounds, a theory known as Mixed Alkali ion Percolation (MAP) theory has been developed [2] and it was shown from x-ray diffraction and conductivity measurements that, at this $f(\beta)$, the potassium ions reside primarily in the $\beta$ phase and the sodium ions occupying sites in the $\beta''$ phase.

The invention contemplates a solid ceramic conductor, of the hydrogen ion, being a solid polycrystalline, with the general formula;

$$(H_3O_a^+/Na_b^+/K_c^+)_2OZ\beta/\beta''Al_2O_3$$

where Z may be occupied by a stabilizer of $\beta''$ and where
$a = 0 \rightarrow 1$
$b = 0 \rightarrow 1$
$c = 0 \rightarrow 1$; and
$a + b + c = 1$ and possessing mobile hydrogen ions in its crystallographic structure that are adapted to move through the ceramic when influenced by an electrical gradient, or by chemically different solutions on opposite boundary surfaces of the ceramic.

The invention further contemplates an active electrochemical element comprising a solid polycrystalline ceramic of the general formula;

$$(H_3O_a^+/Na_b^+/K_c^+)_2OZ\beta/\beta''Al_2O_3$$

whose conductivity to the $H_3O^+$ ion is in the range of $10^{-1}$ to $10^{-3} \Omega^{-1} cm^{-1}$ at 300° C. and its $f(\beta)$ is in the range of $0 \rightarrow 0.55$ wherein $$f(\beta) = \frac{\beta}{\beta + \beta''}$$

and, Z is a predetermined stabilizer of the $\beta''$ phase.

Preferably Z is a compound of magnesium more specifically MgO and preferably the aforesaid general formula reduces to the preferred general formula;

$$(H_3O_a^+/Na_b^+/K_c^+)_2O(3w/oMgO)\beta/\beta''Al_2O_3$$

wherein
$f(\beta) = 0.37 \pm 0.03$
$a = 0 \rightarrow 1$
$b = 0 \rightarrow 1$
$c = 0 \rightarrow 1$
$a + b + c = 1$ The invention further contemplates a method of producing a solid polycrystalline $\beta$ alumina ceramic that is conductive to $H_3O^+$ comprising the steps of;

(a) selecting a sintered solid polycrystalline $\beta$ alumina ceramic with $f(\beta) = 0 \rightarrow 0.55$;

(b) altering the ion distribution of the ceramic by tailoring the lattice size thereof to approximate $34.18 \pm 0.05$ Å; and, (c) immersing the resultant ceramic of step (b) in an acid; while, (d) passing an electrical charge of predetermined quantity through the ceramic whereby to displace certain ions within the ceramic with $H_3O^+$.

The acid may be a dilute acid at a temperature of about 90° C. or concentrated sulfuric acid at 300° C. There are other suitable acids and concentrations as will become apparent.

The predetermined the quantity of charge is determined only by the weight of the sample and the degree of ion exchange desired for the hydronium ion to replace $Na^+$ or $K^+$, or both. Preferably the degree of exchange is 100% of both $Na^+$ and $K^+$.

Preferably the method is supplemented by pre-ionic substitution wherein step (b) further includes the sub steps;

(i) selecting an ionic melt or solution containing two or more ionic species of different ionic radii;

(ii) immersing the selected alumina ceramic of step (a) into the ionic melt until a predetermined amount of cations in the ceramic are displaced by ions of dissimilar size from the ionic solution.

These pre-ionic substitution are preferred to enchance the ultimate $H_3O^+$ conductivity. They in fact increase the crystallographic size of the lattice of the feed ceramic so it is more readily accommodating to the larger $H_3O^+$ ion that in fact replaces, the $Na^+$ and $K^+$ during the step (c).

Specifically the ionic species of the ionic melt or solution are preferably selected from the group of ions $Na^+, K^+, Li^+, H_3O^+$; with mixtures with appropriate anions preferably $Cl^-$, $NO_3^-$, $SO_4^{2-}$ and $COOH^-$. Specifically the polycrystalline ceramic has one or more cations selected from the group $Na^+, K^+, Li^+$ and preferably of the aforesaid chemical formula where the atom fraction of sodium is 0.6; that of potassium 0.4; that of the $\beta$ phase 0.4; and, that of the $\beta''$ phase 0.6.

The invention will now be described by way of example with reference to the accompanying drawings in which.

Figure 4:
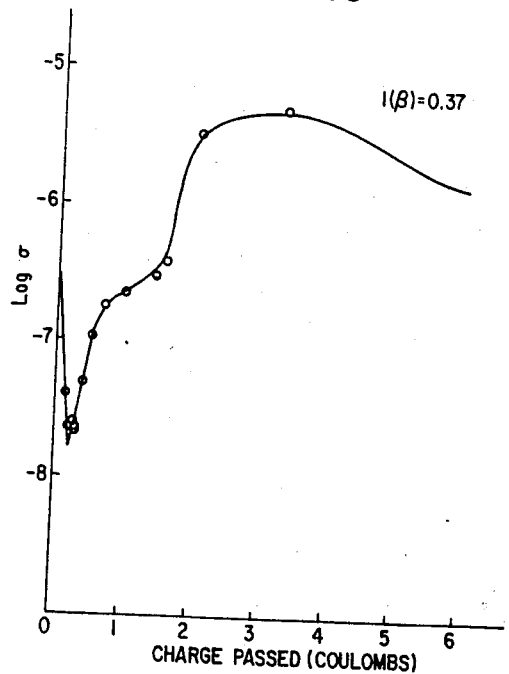
Figure 5:
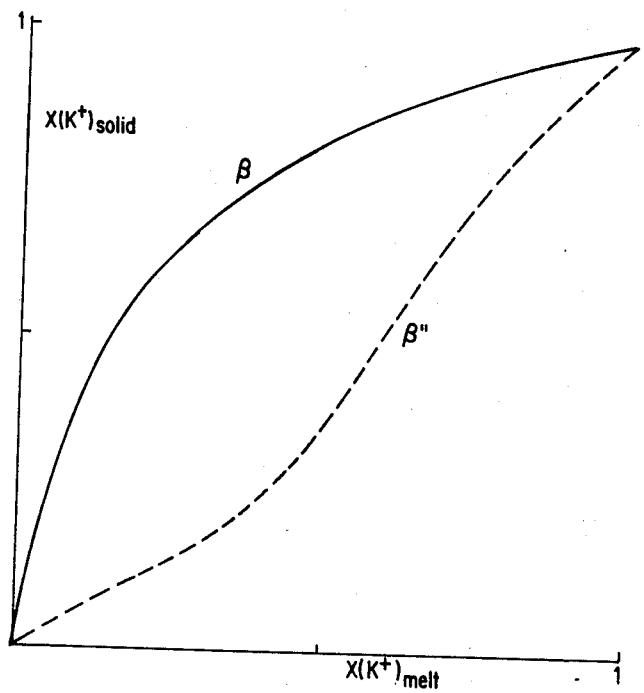
Figure 6:
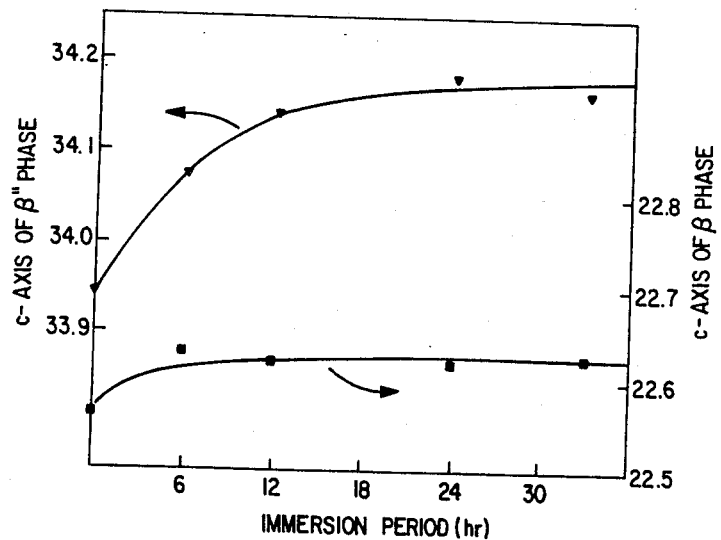

FIG. 4 plots dependence of conductivity (I/V) on charge passed (I.t);

FIG. 5 plots equilibria between $\beta$ and $\beta''$ aluminas and $KNO_3/NaNO_3$ melts at 300° C.;

FIG. 6 plots the variation of the c lattice parameter on immersion in a KCl/NaCl melt at 800° C.

PRELIMINARY TO UNDERSTANDING OF THE INVENTION

Figure 1:
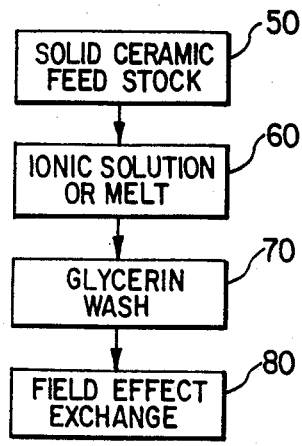
FIG. 1 is a flow chart of the preferred method steps.
Figure 2:
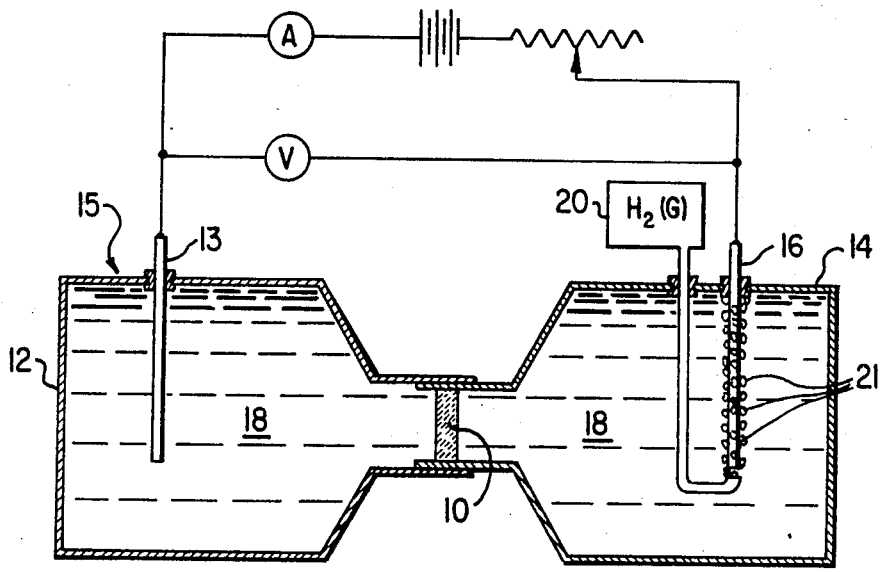
FIG. 2 is an arrangment whereby the method of the invention is performed.
Figure 3:
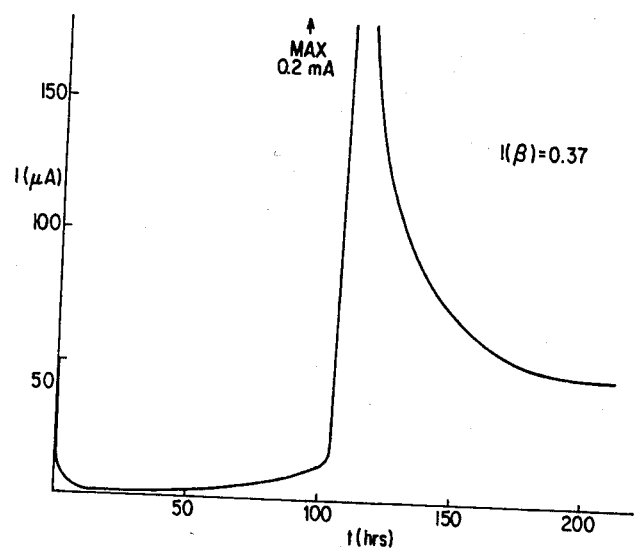
FIG. 3 is a current-time behavior of $\beta$ alumina samples during field assisted ion exchange.

Referring to FIGS. 1 and 2, selected solid polycrystalline $\beta$ alumina ceramics can, when made according to our co-pending applications aforesaid, behave in rather complex ways during ion exchange with the known field assisted technique. The field effect ion exchange is accomplished as follows. A sample ceramic 10 is used to separate two symmetrical compartments 12 and 14 of a glass cell 15. Each of these compartments contained a platinum sheet electrode 13 and 16 immersed in an aqueous mineral or organic acid 18. Reservoir 20 supplies hydrogen gas. Hydrogen gas 21 was bubbled over one electrode 16 throughout the experiment. Ion exchange was carried out by application of a voltage ranging between 1 and 40 volts between these electrodes 13 and 16 and the course of the experiment was followed by measuring the current through the sample and monitoring the pH change in the cathodic compartment. On application of a voltage, the current initially decreases rapidly to approximately 1 μA. However, after around 50 hours, it begins to increase, slowly at first and then very rapidly. A maximum of around 0.2 mA occurs after 100 hours. The conductivity change during the course of this experiment (FIG. 4) shows remarkable similarity to that caused by the mixed alkali effect. (In FIG. 4, the conductivity (I/V) is plotted against the charge passed (I.t) which is proportional to the mole fraction of hydronium ions, $H_3O^+$, in the sample 10.) As the hydronium ion is a univalent ion similar in size to the potassium ion, it is believed that it is behaving like the alkali ion causing a decrease in conductivity due to a preferential occupancy of certain crystallographic sites formly occupied by $Na^+$.

On the basis of the MAP theory disclosed in the copending application filed June 23, 1983, it can be predicted that this problem will be alleviated by introducing a preexchange step to alter the ion distribution and to tailor the lattice size to that of the hydronium ion. The stress induced in this step must be less than the critical strain limit of the ceramic. According to this invention, this aim is achieved by equilibrating suitably prepared polycrystalline material containing one or more cation such as $Na^+$, $K^+$ or $Li^+$ with an ionic melt of solution containing two or more ionic species of differing ionic radii. The composition of the melt or solution can be written as:

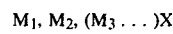

where $M_1$ and $M_2$ (and $M_3$ etc.) are ions of dissimilar size, examples of which are sodium, potassium, lithium and hydronium ions. The concentration of these can be chosen on the basis of literature data of the prior art on the equilibration of $\beta$ alumina with ionic melts or may be determined by experiment. It is noted that the concentration chosen does not depend on the proportion of $\beta$ phase but is calculated on the basis of the desired lattice expansion so as to accommodate the $H_3O^+$ ion size and the fracture strength of the ceramic. In the above formula, X is a suitable anion which does not chemically attack $\beta$ alumina and does not take part in the ion exchange process. Examples for X are $Cl^-$, $NO_3^-$, $SO_4^{2-}$, $COOH^-$ or mixtures of these. The mixture of salts employed may be used to control the temperature at which exchange is carried out. The melt or solution may or may not contain the desired incoming ion. After this treatment, the ceramic may be converted to the desired ionic conductor by ion exchange techniques known.

Thus in the preferred method and referring to FIG. 1, the solid ceramic feed stock 10 according to our co-pending applications is selected 50, then immersed in an ionic solution 60 as aforesaid, washed 70 in glycerin, and then subjected to field effect exchange 80 using the apparatus of FIG. 2.

The following examples further explain the present invention.

EXAMPLE 1

A disc-shaped sample of mixed alkali ion (Na, K) $\beta/\beta''$ alumina prepared according to the previous disclosure and being a polycrystalline of the chemical formula;

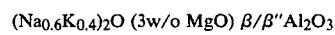

were found to have the following parameters:
atom fraction of sodium=0.6
atom fraction of potassium=0.4
fraction of $\beta$ phase=0.4
fracton of $\beta''$ phase=0.6

As noted earlier, at this fraction of $\beta$ phase, all of the sodium ions (within experimental error) reside in the $\beta''$ phase and thus the lattice parameter of this phase is too small to accommodate the larger hydronium ion. Assuming a linear increase in lattice parameter on going from the sodium to the potassium analogue, calculation suggests that an atom fraction of potassium of 0.59 is required in this phase to accommodate the hydronium ion. Following the work of Kummer [3] (FIG. 4), this can be achieved by immersion in a NaN$_3$O/KNO$_3$ melt with a potassium mole fraction of 0.64. During this step, a small amount of sodium ions also replace potassium ions in the β phase. However the lattice parameter remains sufficiently large to accommodate the hydronium ion.

After the aforesaid ionic procedure, and referring to FIG. 2, the ceramic 10 was converted to the hydronium form by field assisted ion exchange with dilute sulfuric acid (0.1M) at room temperature. It was found that, in contrast to the behavior without the aforesaid pre-exchange substitution step, the current decreased only slowly after an initial rapid decrease and the rate of exchange to the hydronium analogue was a thousand times faster without any evidence of mechanical degradation.

EXAMPLE 2

A similar disc with f(β)=0.56 was immersed in a NaCl/KCl melt (X$_K$=0.64) at 800° C. After each immersion, the sample was subjected to x-ray diffraction analysis. Calculation of the c lattice parameter showed that the equilibration was essentially complete after 24 hours (FIG. 6). It was also noted that, in agreement with the MAP theory, the major lattice expansion occurred in the β phase. After this immersion, the sample was converted to the hydronium form with the field assisted ion exchange technique using dilute acetic acid at 80° C. It was noted that the higher temperature of the exchange step further enhanced the rate of ion exchange.

FOOTNOTES

[1] Also accordingly filed as European Patent Application SN. 82103395.8 filed Apr. 22, 1982, Published Nov. 10, 1982, Bulletin 82/45, as Publication No. A1-0, 064, 226; sub nom Ceramic Hydrogen Ion Conductor and its Preparation.

[2] Bell et al, A Percolation Model for the Conductivity of Mixed Phase, Mixed Ion Alumina, to be published in Solid State Ionics, 1983, disclosed in co-pending Canadian Patent Applications SN. 431,067-5 filed June 23, 1983 entitled THE PREPARATION OF A PRECURSOR SOLID FOR THE MANUFACTURE OF A CERAMIC HYDROGEN ION CONDUCTOR.

[3] J. T. Kummer, Prog. Solid State Chem., 7, 141 (1972).

The embodiments of the invention in which an exclusive property of privilege is claimed are defined as follows:

1. A method of producing a solid polycrystalline β alumina ceramic that is conductive to H$_3$O$^+$ comprising the steps of;
   (a) selecting a sintered solid polycrystalline β alumina ceramic

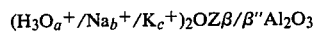

with; f(β)=0→0.55;

(b) altering the ion distribution of the ceramic by tailoring the lattice size thereof to approximate 34.18±0.05 Å; and,
   (c) immersing the resultant ceramic of step (b) in an acid; while,
   (d) passing an electrical charge of predetermined quantity through the ceramic whereby to displace certain ions within the ceramic with H$_3$O$^+$,
   wherein

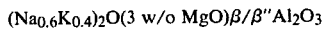

where Z maybe occupied by a stabilizer of the β'' phase and where
   a=0→1;
   b=0→1;
   a+b=1; and
   a+b+c=1.

2. The method as claimed in claim 1, wherein the polycrystaline β alumina ceramic selected in step (a) has the chemical formula;

(Na$_{0.6}$K$_{0.4}$)$_2$O(3 w/o MgO)β/β''Al$_2$O$_3$ and where w/o means weight percentage of the composition.

3. The method as claimed in claim 1, or 2, wherein a voltage greater than 0.1 volts, is employed in step (d).

4. The method as claimed in claim 1, wherein the acid of step (c) is selected from the group of mineral and organic acids.

5. The method as claimed in claim 1, wherein the acid of step (c) is dilute sulfuric, or acetic.

6. The method as claimed in claim 4, wherein the acid is dilute sulfuric with molar concentration 0.1 at room temperature.

7. The method as claimed in claim 4, 5 or 6, wherein the dilute acid is held in the temperature of between room temperature and approximately 80° C.

8. The method a claimed in claim 4, wherein the acid is concentrated sulfuric acid at 300° C.

9. The method as claimed in claim 1, wherein step (b) includes;
   (i) selecting an ionic melt or solution containing two or more ionic species of different ionic radii;
   (ii) immersing the selected alumina ceramic of step (a) into the ionic melt until a predetermined amount of cations in the ceramic are displaced by ions of dissimilar size from the ionic solution.

10. The method as claimed in claim 9, wherein the ionic species of the ionic melt are selected from the group Na$^+$, K$^+$, Li$^+$ and H$_3$O$^+$.

11. The method as claimed in claim 9, wherein the polycrystalline ceramic selected has one or more cations selected from the group of Na$^+$, K$^+$, Li$^+$.

12. The method as claimed in claim 10, wherein the ionic species are in solution with an anion which does not chemically attack β alumina and does not take part in the ion exchange process of step (b).

13. The method as claimed in claim 11, wherein anions are selected from the group of Cl$^-$, NO$_3^-$, SO$_4^{2-}$ and COOH$^-$ or mixtures thereof.

* * * * *